(12) United States Patent
Xu et al.

(10) Patent No.: US 7,122,342 B1
(45) Date of Patent: Oct. 17, 2006

(54) PROTEASE-ACTIVATED RECEPTOR PAR4 (ZCHEMR2)

(75) Inventors: Wen-feng Xu, Mukilteo, WA (US); Scott R. Presnell, Seattle, WA (US); David P. Yee, Seattle, WA (US); Donald C. Foster, Seattle, WA (US)

(73) Assignees: ZymoGenetics, Inc., Seattle, WA (US); University of Washington, Seattle, WA (US)

( * ) Notice: Subject to any disclaimer, the term of this patent is extended or adjusted under 35 U.S.C. 154(b) by 1065 days.

(21) Appl. No.: 09/371,333

(22) Filed: Aug. 10, 1999

Related U.S. Application Data

(62) Division of application No. 09/053,866, filed on Apr. 1, 1998, now Pat. No. 6,111,075.

(51) Int. Cl.
*C12N 15/12* (2006.01)
(52) U.S. Cl. ............... 435/69.1; 435/252.3; 435/320.1; 536/23.5
(58) Field of Classification Search ............... 435/69.1, 435/252.3, 320.1; 530/300; 536/23.5
See application file for complete search history.

(56) References Cited

U.S. PATENT DOCUMENTS 6,436,400 B1    8/2002    Xu et al.

OTHER PUBLICATIONS

Vu et al., "Molecular cloning of a functional thrombin receptor reveals a novel proteolytic mechanism of receptor activation," *Cell* 64:1057-1068, Mar. 22, 1991.
Rasmussen et al., "cDNA cloning and expression of a hamster α-thrombin receptor coupled to $Ca^{2+}$ mobilization," *FEBS Lett.* 288:123-128, Aug., 1991.
Nystedt et al., "Molecular cloning of a potential proteinase activated receptor," *Proc. Nat'l Acad. Sci. USA* 91:9208-9212, Sep. 1994.
Vu et al., "Domains specifying thrombin-receptor interaction," *Nature* 353:674-677, Oct. 17, 1997.
Connolly et al., "Role of the thrombin receptor in development and evidence for a second receptor," *Nature* 381:516-519, Jun. 6, 1996.
Coughlin, "Protease activated receptors start a family," *Proc. Nat'l Acad. Sci. USA* 91:9200-9202, Sep., 1994.
Molino et al., "Endothelial cell thrombin receptors and PAR-2," *J. Biol. Chem.* 272:11133-11141, Apr. 25, 1997.
Gerszten et al., "Specificity of the thrombin receptor for agonist peptide is defined by its extracellular surface," *Nature* 368:648-651, Apr, 14, 1994.
Ishii et al., "Inhibition of thrombin receptor signaling by a G-protein coupled receptor kinase," *J. Biol. Chem.* 269:1125-1130, Jan. 14, 1994.
Probst et al., "Sequence alignment of the G-protein coupled receptor superfamily," *DNA Cell Biol.* 11:1-20, 1997.
Ishihara et al., "Protease-activated receptor 3 is a second thrombin receptor in humans," *Nature* 386:502-506, Apr. 3, 1997.
EST from Incyte Pharmaceuticals, Inc., 373881.
EST from Incyte Pharmaceuticals, Inc., 2189250.
EST from Incyte Pharmaceuticals, Inc., 2899749.
EST from Incyte Pharmaceuticals, Inc., 3218437.
U.S. Appl. No. 09/480,720 filed Jan. 07, 2002, Xu et al.
U.S. Appl. No. 10/187,049 filed Jun.28, 2002, Xu et al.

*Primary Examiner*—John Ulm
(74) *Attorney, Agent, or Firm*—Michelle L. Lewis; Phillip B. D. Jones

(57) ABSTRACT

The present invention relates to polynucleotide and polypeptide molecules for PAR4, a novel member of the protease-activated receptor family. The polypeptides, and polynucleotides encoding them, mediate biological responses and/or cellular signaling in response to proteases. Protease cleavage of PAR4 exposes a PAR4 extracellular amino terminal portion that serves as a ligand for the PAR4 receptor. PAR4 may be used as a target in drug screening, and further used to identify proteinaceous or non-proteinaceous PAR4 agonists and antagonists. The present invention also includes antibodies to the PAR4 polypeptides.

23 Claims, 1 Drawing Sheet

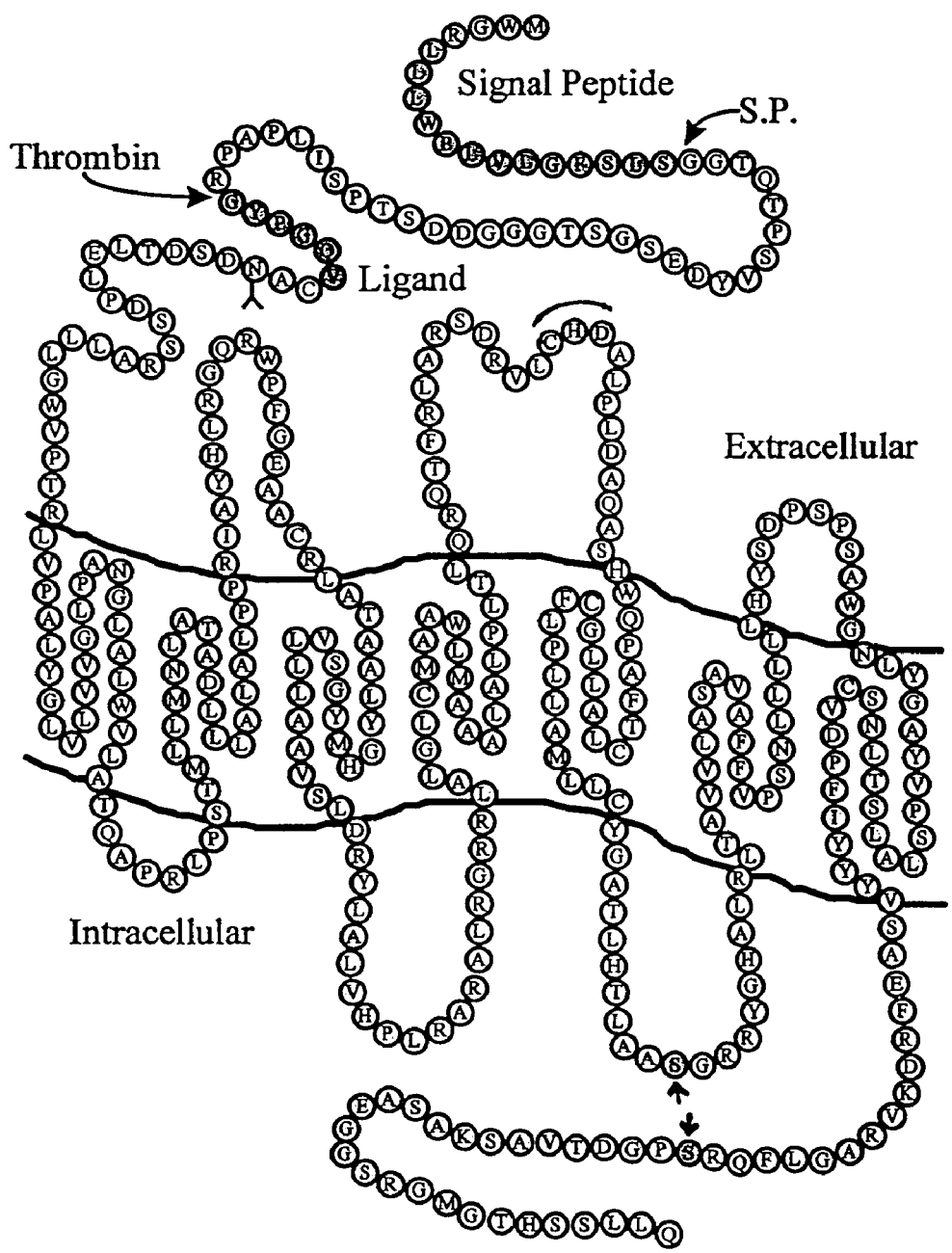
FIGURE

# PROTEASE-ACTIVATED RECEPTOR PAR4 (ZCHEMR2)

This is a divisional application of application Ser. No. 09/053,866, filed Apr. 1, 1998 now U.S. Pat. No. 6,111,075.

STATEMENT REGARDING FEDERALLY SPONSORED RESEARCH OR DEVELOPMENT

The government may have certain rights in this application by virtue of federal funding under Grant No. 5 R01 HL15919-23 (National Institutes of Health).

BACKGROUND OF THE INVENTION

An intriguing question in cell biology relates to the mechanism(s) by which proteases activate cells. In recent years, a subfamily of G protein-coupled receptors capable of mediating cellular signaling in response to proteases has been identified (T. K. H. Vu et al, *Cell* 64:1057–68, 1991; U. B. Rasmussen et al. *FEBS Lett.* 288:123–28, 1991; S. Nystedt et al., *Proc. Natl. Acad. Sci. USA* 91:9208–12, 1994; H. Ishihara et al., *Nature* 353:674–77, 1997). Members of this unique G protein-coupled receptor family include protease-activated receptors PAR1, PAR2 and PAR3. These receptors are characterized by a tethered peptide ligand at the extracellular amino terminus that is generated by minor proteolysis.

The first identified member of this family was the thrombin receptor presently designated protease-activated receptor 1 (PAR1). Thrombin cleaves an amino-terminal extracellular extension of PAR1 to create a new amino terminus that functions as a tethered ligand and intramolecularly activates the receptor (T. K. H. Vu et al, *Cell* 64:1057–68, 1991). PAR2 mediates signaling following minor proteolysis by trypsin or tryptase, but not thrombin (S. Nystedt et al., *Proc. Natl. Acad. Sci. USA* 91:9208–12, 1994). Knockout of the gene coding for PAR1 provided definitive evidence for a second thrombin receptor in mouse platelets and for tissue-specific roles for different thrombin receptors (A. Connolly et al., *Nature* 381:516–19, 1996). PAR3 was identified recently as a second thrombin receptor mediates phosphatidyl inositol 4,5 diphosphate hydrolysis, and was found to be expressed in a variety of tissues (H. Ishihara et al., *Nature* 353:674–77, 1997). Many other proteases (such as factor VIIa, factor Xa, factor XIIa, protein C, neutrophil cathepsin G, mast cell tryptase, and plasmin) display cellular effects. Therefore, additional members of the PAR family are expected to exist (S. R. Coughlin, *Proc. Natl. Acad. Sci. USA* 91:9200–02, 1994; M. Molino et al., *J. Biol. Chem.* 272:11133–41, 1997).

The present invention provides an additional member of the PAR family, a novel human protease-activated receptor designated PAR4 (alternatively designated ZCHEMR2). The PAR4 polypeptide is an appropriate target for drug screening, and has other uses that should be apparent to those skilled in the art from the teachings herein.

SUMMARY OF THE INVENTION

The present invention provides a novel human protease activated receptor polypeptide and related compositions and methods.

Within one aspect, the present invention provides an isolated polynucleotide encoding a PAR4 polypeptide selected from the group consisting of (a) polynucleotide molecules comprising a nucleotide sequence as shown in SEQ ID NO:1 from nucleotide 176 to nucleotide 1330; (b) allelic variants of (a); (c) orthologs of (a); and (d) degenerate nucleotide sequences of (a), (b) or (c). In one embodiment, the polynucleotide molecules comprise a nucleotide sequence as shown in SEQ ID NO: 1 from nucleotide 227 to nucleotide 1330. In another embodiment, the polynucleotide molecules comprise a nucleotide sequence as shown in SEQ ID NO: 1 from nucleotide 317 to nucleotide 1330.

Within another aspect, the present invention provides an isolated polynucleotide molecule encoding a PAR4 ligand selected from the group consisting of (a) polynucleotide molecules comprising a nucleotide sequence as shown in SEQ ID NO: 1 from nucleotide 317 to nucleotide 409; (b) allelic variants of (a); (c) orthologs of (a); and (d) degenerate nucleotide sequences of (a), (b) or (c).

Within yet another aspect, there is provided an expression vector comprising the following operably linked elements a transcription promoter; a DNA segment selected from the group consisting of (a) polynucleotide molecules comprising a nucleotide sequence as shown in SEQ ID NO:1 from nucleotide 176 to nucleotide 1330; (b) allelic variants of (a); (c) orthologs of (a); and (d) degenerate nucleotide sequences of (a), (b) or (c); and a transcription terminator. The present invention also provides a cultured cell into which has been introduced such expression vector, wherein the cell expresses the PAR4 polypeptide.

Within a further aspect, the invention provides an isolated PAR4 polypeptide selected from the group consisting of (a) polypeptide molecules comprising an amino acid sequence as shown in SEQ ID NO: 2 from residue 18 (Gly) to residue 385 (Gln); (b) allelic variants of (a); and (c) orthologs of (a), wherein the PAR4 polypeptide is a protease-activated receptor.

The invention further provides an isolated PAR4 ligand selected from the group consisting of (a) polypeptide molecules comprising an amino acid sequence as shown in SEQ ID NO:2 from residue 48 (Gly) to residue 53 (Val); (b) allelic variants of (a); and (c) orthologs of (a), as well as a pharmaceutical composition comprising purified PAR4 ligand in combination with a pharmaceutically acceptable vehicle. Another aspect of the invention provides an antibody that binds to an epitope of a PAR4 polypeptide.

These and other aspects of the invention will become evident upon reference to the following detailed description of the invention and attached drawings.

BRIEF DESCRIPTION OF THE DRAWINGS

The FIGURE depicts the predicted seven transmembrane organization of PAR4. The signal peptide is located N-terminal of the signal peptidase cleavage site (denoted "S.P."), and is shaded. The amino terminal peptide cleaved by thrombin is located between the S.P. cleavage site and the thrombin cleavage site (denoted "Thrombin"). A 6 amino acid tethered peptide ligand is situated C-terminal of the thrombin cleavage site and is shaded. The CHD sequence in the second transmembrane loop is located at the upper right of the second extracellular loop (designated with a bar). A potential serine phosphorylation site for protein kinase C in the sequence SGR (in the third intracellular loop), and a potential phosphorylation site for protein kinase II in the sequence SPGD (in the C-terminal extracellular domain), are indicated by shading and arrows. Y indicates a potential carbohydrate binding site.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complement of a polynucleotide molecule" denotes a polynucleotide molecule having a complementary base sequence and reverse orientation as compared to a reference sequence. For example, the sequence 5' ATG-CACGGG 3' (SEQ ID NO:13) is complementary to 5' CCCGTGCAT 3' (SEQ ID NO:14).

The term "contig" denotes a polynucleotide that has a contiguous stretch of sequence that is identical or complementary to that of another polynucleotide. Contiguous sequences are said to "overlap" a given stretch of polynucleotide sequence, either in their entirety or along a partial stretch of the polynucleotide. For example, representative contigs to the polynucleotide sequence 5'-ATGGTTAGCTT-3' (SEQ ID NO:15) are 5'-TAGCTTgagtct-3' (SEQ ID NO:16) and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see, for example, Dynan and Tijan, *Nature* 316:774–78, 1985).

An "isolated polypeptide or isolated protein" is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules, it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus, all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure (also sometimes referred to as a "multi-peptide", wherein subunit binding and signal transduction can be functions of separate subunits) comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a polypeptide having the structure of a seven transmembrane domain protein that features an open reading frame of 385 amino acids. This polypeptide, designated PAR4 or ZCHEMR2, has about 33% amino acid sequence identity with PAR1, PAR2 or PAR3. A putative serine protease cleavage site (R47/G48) was identified within the extracellular amino terminal portion of the polypeptide.

Analysis of the tissue distribution of the mRNA corresponding to this PAR4 polynucleotide showed that expression was highest in lung, pancreas, thyroid, testis and small intestine. Moderate expression of PAR4 was observed in prostate, placenta, skeletal muscle, lymph node, adrenal gland, uterus and colon. PAR4 mRNA was also detected in human platelets by RT-PCR, but the level of this expression was less than that of PAR1. No expression of PAR4 was detected in brain, kidney, spinal cord or peripheral blood leukocytes.

The novel PAR4 polypeptides of the present invention were initially identified by querying an EST database for sequences homologous to PAR1, PAR2 and/or PAR3. An EST sequence was identified, and matched a sequence of the three known PARs in a portion of the fourth transmembrane domain. The deduced amino acid sequence corresponding to this EST sequence shared 34% identity with the PAR2 amino acid sequence in the transmembrane region. A full length cDNA clone (4.9 kb) corresponding to this EST was isolated from a size-selected lymphoma Daudi cell cDNA library.

The nucleotide sequence of PAR4 (ZCHEMR2) is described in SEQ ID NO:1; its deduced amino acid sequence is described in SEQ ID NO:2; and its corresponding degenerate DNA sequence is described in SEQ ID NO:3. The polynucleotide sequence within the full length clone included an open reading frame encoding a 385 amino acid protein (1155 nucleotides, from nucleotide 176 to nucleotide 1330), including a 17 amino acid signal peptide (amino acid residues M1 to S17, corresponding to nucleotide 176 to nucleotide 226). In addition, SEQ ID NO:1 describes 175 nucleotides of 5'-untranslated region (nucleotide 1 to nucleotide 175), and a long GC-rich 3'-untranslated region containing several polyadenylation signals and a poly(A) tail (3565 nucleotides; from nucleotide 1331 to nucleotide 4895).

A hydropathy plot of the amino acid sequence of SEQ ID NO:2 showed that the receptor is a member of the seven transmembrane domain receptor family. A hydrophobic signal sequence was identified, having a potential signal peptidase cleavage site at S17/G18. A putative cleavage site for protease activation at R47/G48 was also located within the extracellular amino terminus portion of the polypeptide. The extracellular amino terminus and the intracellular carboxy terminus of PAR4 have little or no amino acid sequence homology to the corresponding regions of the three known PARs. Further, the protease cleavage site in PAR2 is substantially different from that in PAR1, PAR2 and PAR3, as shown in Table 1.

TABLE 1

Protease Cleavage Sites in PAR1, PAR2 PAR3 and PAR 4.

| | |
|---|---|
| PAR1 (37–61) | TLDPR↓*SFLLRN*PNDKYEP<u>FWEDE</u>EK (SEQ ID NO:18) |
| PAR2 (32–56) | SSKGR↓*SLIGKV*DGTSHVTGKGVTVE (SEQ ID NO:19) |
| PAR3 (34–57) | TLPIK↓TFRGAPPN S<u>FEEF</u>PFSALE (SEQ ID NO:20) |
| PAR4 (28–52) | LPAPR↓*GYPGQV*CANDSDTLELPDSS (SEQ ID NO:21) |

Regions important for fibrinogen anion exosite binding in thrombin are underlined.

In the second extracellular loop, PAR4 has only three amino acids (CHD) that match the sequence of ITTCHDV (SEQ ID NO:4) that is conserved in PAR1, PAR2 and PAR3. The second extracellular loop is important in determining specificity of PAR1 from human and *X. laevis* sources for their respective activating peptides (R. E. Gerszten et al., *Nature* 368:548–51, 1994).

The present invention also provides polynucleotide molecules, including DNA and RNA molecules, that encode the PAR4 polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the PAR4 polypeptide of SEQ ID NO:2. Those skilled in the art will recognize that the degenerate sequence of SEQ ID NO:3 also provides all RNA sequences encoding SEQ ID NO:2 by substituting U for T. Thus, PAR4 polypeptide-encoding polynucleotides comprising nucleotide 1 to nucleotide 1330 of SEQ ID NO:1 and their RNA equivalents are contemplated by the present invention. Table 2 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 2

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 3.

TABLE 3

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

It is to be recognized that, according to the present invention, when a polynucleotide is claimed as described herein, it is understood that what is claimed are both the sense strand, the anti-sense strand, and the DNA as double-stranded having both the sense and anti-sense strand annealed together by their respective hydrogen bonds. Also claimed is the messenger RNA (mRNA) which encodes the polypeptides of the present invention, and which mRNA is encoded by the cDNA described herein. Messenger RNA (mRNA) will encode a polypeptide using the same codons as those defined herein, with the exception that each thymine nucleotide (T) is replaced by a uracil nucleotide (U).

One of ordinary skill in the art will also appreciate that different species can exhibit "preferential codon usage." In general, see Grantham et al., *Nucl. Acids Res.* 8:1893–912, 1980; Haas et al., *Curr. Biol.* 6:315–24, 1996; Wain-Hobson et al., *Gene* 13:355–64, 1981; Grosjean and Fiers, *Gene* 18:199–209, 1982; Holm, *Nucl. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 3).

For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of PAR4 RNA. Such tissues and cells are identified by Northern blotting (Thomas, *Proc. Natl. Acad. Sci. USA* 77:5201, 1980), and include a lymphoma Daudi cell line, lung, pancreas, thyroid, testis and small intestine. Total RNA can be prepared using guanidine HCl extraction followed by isolation by centrifugation in a CsCl gradient (Chirgwin et al., *Biochemistry* 18:52–94, 1979). Poly (A)⁺ RNA is prepared from total RNA using the method of Aviv and Leder (*Proc. Natl. Acad. Sci. USA* 69:1408–12, 1972). Complementary DNA (cDNA) is prepared from poly(A)⁺ RNA using known methods. In the alternative, genomic DNA can be isolated. Polynucleotides encoding PAR4 polypeptides are then identified and isolated by, for example, hybridization or PCR.

A full-length clone encoding PAR4 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to PAR4, PAR4 fragments, or other specific binding partners.

The present invention further provides counterpart polypeptides and polynucleotides from other species (orthologs). These species include, but are not limited to mammalian, avian, amphibian, reptile, fish, insect and other vertebrate and invertebrate species. Of particular interest are PAR4 polypeptides from other mammalian species, including murine, porcine, ovine, bovine, canine, feline, equine, and other primate polypeptides. Orthologs of human PAR4 polypeptides can be cloned using information and compositions provided by the present invention in combination with conventional cloning techniques. For example, a cDNA can be cloned using mRNA obtained from a tissue or cell type that expresses PAR4 as disclosed herein. Suitable sources of mRNA can be identified by probing Northern blots with probes designed from the sequences disclosed herein. A library is then prepared from mRNA of a positive tissue or cell line. A PAR4-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human PAR4 sequence disclosed herein. Within an additional method, the cDNA library can be used to transform or transfect host cells, and expression of the cDNA of interest can be detected with an antibody to PAR4 polypeptide. Similar techniques can also be applied to the isolation of genomic clones.

Those skilled in the art will recognize that the sequence disclosed in SEQ ID NO:1 represents a single allele of human PAR4 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the PAR4 polypeptides are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated PAR4 polypeptides that are substantially homologous to the polypeptides of SEQ ID NO:2 and their orthologs. The term "substantially homologous" is used herein to denote polypeptides having 50%, preferably 60%, more preferably at least 80%, sequence identity to the sequences shown in SEQ ID NO:2 or their orthologs. Such polypeptides will more preferably be at least 90% identical, and most preferably 95% or more identical to SEQ ID NO:2 or its orthologs. Percent sequence identity is determined by conventional methods. See, for example, Altschul et al., *Bull. Math. Bio.* 48:603–16, 1986; and Henikoff and Henikoff, *Proc. Natl. Acad. Sci. USA* 89:10915–19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.), as shown in Table 4 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 4

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Variant PAR4 polypeptides or substantially homologous PAR4 polypeptides are characterized as having one or more amino acid substitutions, deletions or additions. These changes are preferably of a minor nature, that is conservative amino acid substitutions (see Table 5) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag. The present invention thus includes polypeptides of from 6 to 410 [385+25] amino acid residues that comprise a sequence that is at least 50%, preferably at least 80%, and more preferably 90% or more identical to the corresponding region of SEQ ID NO:2. Polypeptides comprising affinity tags can further comprise a proteolytic cleavage site between the PAR4 polypeptide and the affinity tag. Preferred such sites include thrombin cleavage sites and factor Xa cleavage sites.

TABLE 5

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other PAR4 fragment fusions, and related chimeric or hybrid PAR4 polypeptides or fragments. For example, a PAR4 fragment can be prepared as a fusion to a dimerizing protein, as disclosed in U.S. Pat. Nos. 5,155,027 and 5,567,584. Preferred dimerizing proteins in this regard include immunoglobulin constant region domains. Immunoglobulin-PAR4 fragment fusions can be expressed in genetically engineered cells to produce a variety of multimeric PAR4 fragment analogs. Auxiliary domains can be fused to PAR4 fragment to target them to specific cells, tissues, or macromolecules (e.g., collagen). For example, a PAR4 fragment could be targeted to a predetermined cell type by fusing a PAR4 fragment to a non-PAR4 moiety such that the fusion protein specifically binds to a receptor on the surface of the target cell. In this way, polypeptides and proteins can be targeted for therapeutic or diagnostic purposes. A PAR4 fragment can be fused to two or more moieties, such as an affinity tag for purification and a targeting domain. Fragment fusions can also comprise one or more cleavage sites, particularly between domains. See Tuan et al., *Connective Tissue Research* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Meth. Enzymol.* 202:301, 1991; Chung et al., *Science* 259:806–09, 1993; and Chung et al., *Proc. Natl. Acad. Sci. USA* 90:10145–49, 1993). In a second method, translation is carried out in *Xenopus* oocytes by microinjection of mutated mRNA and chemically aminoacylated suppressor tRNAs (Turcatti et al., *J. Biol. Chem.* 271:19991–98, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–76, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for PAR4 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–85, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of ligand-receptor or agonist/antagonist-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related PAR family members.

Multiple amino acid substitutions can be made and tested using known methods of mutagenesis and screening, such as those disclosed by Reidhaar-Olson and Sauer (*Science* 241: 53–57, 1988) or Bowie and Sauer (*Proc. Natl. Acad. Sci. USA* 86:2152–56, 1989). Briefly, these references disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–37, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed PAR4 DNA and polypeptide sequences can be generated through DNA shuffling, as disclosed by Stemmer, *Nature* 370:389–91, 1994; Stemmer, *Proc. Natl. Acad. Sci. USA* 91:10747–51, 1994; and WIPO Publication WO 97/20078. Briefly, variant DNAs are generated by in vitro homologous recombination by random fragmentation of a parent DNA, followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay, provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., those activated by proteases; those that mediate a biological response in the presence of proteases; those that stimulate the PAR4 receptor itself) can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptide fragments or variants of SEQ ID NO:2 that retain the PAR family properties of the wild-type PAR4 protein. Such polypeptides may include a complete extracellular amino terminus portion; an extracellular amino terminus portion corresponding to amino acid residues G18 through G48, or to amino acid residues G18 through R78, or to amino acid residues G48 through R78; an extracellular portion linked to one or more of the seven transmembrane domains of PAR4; and the like.

For any PAR4 polypeptide, including variants and fusion proteins, one of ordinary skill in the art can readily generate a fully degenerate polynucleotide sequence encoding that variant using the information set forth in Tables 2 and 3, above.

The PAR4 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989; and Ausubel et al., eds., *Current Protocols in Molecular Biology*, John Wiley and Sons, Inc., NY, 1987.

In general, a DNA sequence encoding a PAR4 polypeptide or a portion thereof is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a PAR4 polypeptide or fragment into the secretory pathway of a host cell, a secretory signal sequence (also known as a leader sequence, prepro sequence or pre sequence) is provided in the expression vector. The secretory signal sequence may be that of the native PAR4 polypeptide, or may be derived from another secreted protein (e.g., t-PA) or synthesized de novo. The secretory signal sequence is operably linked to the PAR4 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residues M1 to S17 of SEQ ID NO:2 is operably linked to another polypeptide using methods known in the art and disclosed herein. The secretory signal sequence contained in the fusion polypeptides of the present invention is preferably fused amino-terminally to a second peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–45, 1982), DEAE-dextran mediated transfection (Ausubel et al., ibid.), liposome-mediated transfection (Hawley-Nelson et al., *Focus* 15:73, 1993; Ciccarone et al., *Focus* 15:80, 1993), and viral vectors (Miller and Rosman, *BioTechniques* 7:980–90, 1989; Wang and Finer, *Nature Med.* 2:714–16, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g., CHO-$K_1$; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins, such as CD4, CD8, Class I MHC, placental alkaline phosphatase, may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding the PAR4 polypeptide is inserted into the baculoviral genome in place of the AcNPV polyhedrin gene coding sequence by one of two methods. The first is the traditional method of homologous DNA recombination between wild-type AcNPV and a transfer vector containing the PAR4 polynucleotide flanked by AcNPV sequences. Suitable insect cells, e.g., SF9 cells, are infected with wild-type AcNPV and transfected with a transfer vector comprising a PAR4 polynucleotide operably linked to an AcNPV polyhedrin gene promoter, terminator, and flanking sequences. See, L. A. King and R. D. Possee, *The Baculovirus Expression System: A Laboratory Guide*, London, Chapman & Hall; D. R. O'Reilly et al., *Baculovirus Expression Vectors: A Laboratory Manual*, New York, Oxford University Press., 1994; and, C. D. Richardson, ed., *Baculovirus Expression Protocols. Methods in Molecular Biology*, Totowa, N.J., Humana Press, 1995. Natural recombination within an insect cell will result in a recombinant baculovirus which contains PAR4 driven by the polyhedrin promoter. Recombinant viral stocks are made by methods commonly used in the art.

The second method of making recombinant baculovirus utilizes a transposon-based system described by Luckow (V. A. Luckow et al., *J. Virol.* 67:4566–79, 1993). This system is sold in the Bac-to-Bac kit (Life Technologies, Rockville, Md.). This system utilizes a transfer vector, pFastBacI™ (Life Technologies), containing a Tn7 transposon to move the DNA encoding the PAR4 polypeptide into a baculovirus genome maintained in *E. coli* as a large plasmid called a "bacmid." The pFastBacI™ transfer vector utilizes the AcNPV polyhedrin promoter to drive the expression of the gene of interest, in this case PAR4. However, pFastBacI™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, M. S. Hill-Perkins and R. D. Possee, *J. Gen. Virol.* 71:971–76, 1990; B. C. Bonning et al., *J. Gen. Virol.* 75:1551–56, 1994; and G. D. Chazenbalk and B. Rapoport, *J. Biol. Chem.* 270:1543–49, 1995. In such transfer vector constructs, a short or long version of the basic protein promoter can be used. Moreover, transfer vectors can be constructed which replace the native PAR4 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native PAR4 secretory signal sequence. In addition, transfer vectors can include an in-frame fusion with DNA encoding an epitope tag at the C- or N-terminus of the expressed PAR4 polypeptide, for example, a Glu—Glu epitope tag (T. Grussenmeyer et al., *Proc. Natl. Acad. Sci. USA* 82:7952–54, 1985). Using a technique known in the art, a transfer vector containing PAR4 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g., Sf9 cells. Recombinant virus that expresses PAR4 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High Five™ cell line (Invitrogen) derived from *Trichoplusia ni* (U.S. Pat. No. 5,300,435). Commercially available serum-free media are used to grow and maintain the cells. Suitable media include Sf900 II™ (Life Technologies) or ESF921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells, at which time a recombinant viral stock is added at a multiplicity of infection (MOI) of 0.1 to 10, more typically near 3. The recombinant virus-infected cells typically produce the recombinant PAR4 polypeptide at 12–72 hours post-infection and secrete it with varying efficiency into the medium. The culture is usually harvested 48 hours post-infection. Centrifugation is used to separate the cells from the medium (supernatant). The supernatant containing the PAR4 polypeptide is filtered through micropore filters, usually 0.45 μm pore size. Procedures used are generally described in available laboratory manuals (L. A. King and R. D. Possee, ibid.; D. R. O'Reilly et al., ibid.; C. D. Richardson, ibid.). Subsequent purification of the PAR4 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharonyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459–65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli*, *Bacillus* and other genera are also useful host cells within the present invention. Techniques for transforming these hosts and expressing foreign DNA sequences cloned therein are well known in the art (see, e.g., Sambrook et al., ibid.). When expressing a PAR4 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify PAR4 polypeptide fragments or fusions (particularly those that function as PAR4 agonists or antagonists) to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified PAR4 polypeptide fragment or fusion is substantially free of other polypeptides, particularly other polypeptides of animal origin.

Expressed recombinant PAR4 polypeptide fragments, PAR4 fragment fusions, or PAR4 fragment chimeras or hybrids can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The PAR4 polypeptide fragments, PAR4 fragment fusions or PAR4 fragment chimeric or hybrid polypeptides of the present invention can be isolated by exploitation of PAR family properties. For example, immobilized metal ion adsorption (IMAC) chromatography can be used to purify PAR4 polypeptides or fragments that comprise a polyhistidine tag. Briefly, a gel is first charged with divalent metal ions to form a chelate (Sulkowski, *Trends in Biochem.* 3:1–7, 1985). Histidine-rich or -tagged proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529–39). Within additional embodiments of the invention, a fusion of the polypeptide or fragment of interest and an affinity tag (e.g., maltose-binding protein, an immunoglobulin domain) may be constructed to facilitate purification.

Components of the PAR4 polypeptide may be combined with other G protein-coupled receptor components to form chimeric or hybrid G protein-coupled receptors. Alternatively, such hybrid or chimeric receptors may include a component of PAR4 from one species and a second component of PAR4 from another species (see, for example, U.S. Pat. No. 5,284,746). More specifically, using regions or domains of the inventive PAR4 protein or fragments thereof in combination with those of other human PAR family proteins or heterologous PAR proteins (Sambrook et al., ibid.; Altschul et al., ibid.; Picard, *Curr. Opin. Biology* 5:511–15, 1994, and references therein), hybrid or chimeric PAR4 polypeptides or fragments may be obtained through recombinant means (or in the case of fragments, may be synthesized). Construction of these polypeptides allows the determination of the biological importance of larger domains or regions in a polypeptide of interest. Such hybrids may modulate reaction kinetics or binding, may constrict or expand the substrate specificity, or may alter tissue and cellular localization of a polypeptide, and can be applied to polypeptides of unknown structure. For G protein-coupled receptors, the chimeric or hybrid polypeptides may be less than full length (for instance, may include none, one or more transmembrane domains; may include only extracellular portions; and the like).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between the PAR4 polypeptide or fragment of the present invention with the functionally equivalent domain(s) from another family member, such as PAR1, PAR2 or PAR3. Such domains include, but are not limited to, the secretory signal sequence, the extracellular N-terminal domain, an extracellular loop, a transmembrane region, an intracellular loop, or the intracellular C-terminal domain. Such fusion proteins would be expected to have a biological and functional profile that is the same or similar to polypeptides of the present invention or other known G protein-coupled receptor and/or PAR family proteins, depending on the fusion constructed. Moreover, such fusion proteins may exhibit other properties, as disclosed herein.

PAR4 polypeptides or fragments thereof may also be prepared through chemical synthesis. PAR4 polypeptides or fragments may be monomers or multimers; glycosylated or non-glycosylated; pegylated or non-pegylated; and may or may not include an initial methionine amino acid residue.

The activity of molecules of the present invention can be measured using a variety of assays that measure cellular activation or responses (including platelet activation, adhesion or aggregation), signaling events, ligand binding or receptor agonism or antagonism. Of particular interest are assays involving phosphoinositide hydrolysis; mobilization of intracellular calcium; modification of ligand with active site inhibitors; mutation of ligand active site residues; ligand antagonists; affinity tag release following proteolysis; and protease substrate/cleavage product determinations. Such assays are well known in the art. For a general reference, see T. K. H. Vu et al., *Cell* 64:1057–68, 1991; or H. Ishihara et al., *Nature* 386:502–06, 1997.

Proteins of the present invention are useful for studying the effects of ligand-receptor interactions on cellular activation and responses in vitro and in vivo. In addition, the PAR4 polypeptide, fragment or chimeric polypeptide of the present invention may be useful in screening for receptor agonists and antagonists. PAR4 activities can be measured in vitro using cultured cells transfected with the PAR4 polypeptide, or in vivo by administering soluble PAR4 fragments (for instance, portions of the N-terminal extracellular region) or PAR4 fusion polypeptides of the claimed invention to the appropriate animal model.

An alternative in vivo approach for assaying proteins or fragments of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

PAR4 agonists and antagonists have enormous potential in both in vitro and in vivo applications. Compounds identified as PAR4 agonists are useful for up-regulating cellular responses and physiology; PAR4 antagonists are useful for down-regulating these same activities. In addition, the PAR4 polypeptides and fragments may be used to dissect the effects of thrombin (a serine protease) or other activating proteases in the clotting pathway from the effects of thrombin or other activating proteases at the cellular level. Further, PAR4 agonist compounds are useful as components of defined cell culture media for growth of cells expressing PAR4 and stimulated by protease cleavage and activation of PAR4. PAR4 fragments or agonists may be used alone or in combination with other cytokines, hormones and the like to replace serum that is commonly used in cell culture. PAR4 agonists are thus useful in specifically promoting the proliferation and/or differentiation of platelets; in mediating inflammatory events, responses to vascular injury, chemotaxis or mitogenesis; and in promoting production of growth factors.

PAR4 antagonists are also useful as research reagents for characterizing sites of ligand-receptor interaction. Antibodies directed against PAR4 polypeptides and fragments may also serve as useful antagonists for in vitro and in vivo studies and administration. More specifically, anti-PAR4 antibodies or PAR4 antagonists may selectively inhibit the cellular effects of thrombin or other activating proteases, while leaving the clotting pathway fully responsive to thrombin. PAR4 antagonists may also be useful for down-regulating biological responses or activities of cells that overproduce PAR4 or that exhibit increased intracellular signaling in response to PAR4 stimulation. This down-regulation may be particularly useful for prophylaxis or treatment of recipients suffering from a disease or syndrome wherein responsive cells (such as platelets) are overproduced or are abnormally up-regulated. If the PAR4 antagonist is capable of being targeted to and/or localized in specific tissues or organs (such as with fusion polypeptides having a targeting component), selective decreases in cellular activities or responses may be obtained. Soluble PAR4 extracellular domains may also be useful as antagonists.

PAR4 agonists and antagonists may be proteinaceous or non-proteinaceous, and may include peptidic and non-peptidic agents (including ribozymes), small molecules and mimetics. PAR4 agonists and antagonists may also be useful in determining the specificity, activities and distribution of other PAR family members, as well as in examining the roles played by intracellular signaling components (such as the variety of G proteins present in cells) with respect to these PAR family members (and, more broadly, with respect to G protein-coupled receptor family members).

PAR4 activation may be studied by determining phosphoinositide hydrolysis after protease stimulation. Site-directed mutagenesis is advantageously used to evaluate protease cleavage (activation) sites in PAR4 polypeptides. Synthetic peptides derived from the unmasked amino terminus of PAR4 following protease cleavage are also useful in studying PAR4 activation. Intracellular phosphorylation sites can be examined for their involvement in termination of signaling by PAR4. An epitope-tagged PAR4 assay also provides information about cleavage and activation of PAR4.

Mammalian cells transfected with PAR4 constructs are useful systems for studying activating peptides, agonists and antagonists of PAR4. A PAR4 transfected cell is used to screen for ligands for the receptor, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptors are selected and used within a variety of screening systems.

Cells expressing functional PAR4 are used within screening assays. A variety of suitable assays are known in the art. These assays are based on the detection of a biological response in a target cell. An increase in metabolism above a control value indicates a test compound that modulates PAR4 activity or responses. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65:55–63, 1983). An additional assay method involves measuring the effect of a test compound on receptor (+) cells, containing the receptor of interest on their cell surface, and receptor (−) cells, those which do not express the receptor of interest. These cells can be engineered to express a reporter gene. The reporter gene is linked to a promoter element or response element that is responsive to the receptor-linked pathway, and the assay detects activation of transcription of the reporter gene. Suitable response elements include cyclic AMP response elements (CRE), hormone response elements (HRE), insulin response elements (IRE) (Nasrin et al., *Proc. Natl. Acad. Sci. USA* 87:5273–77, 1990), and serum response elements (SRE) (Shaw et al., *Cell* 56: 563–72, 1989). Cyclic AMP response elements are reviewed in Roestler et al., *J. Biol. Chem.* 263 (19):9063–66; 1988; and Habener, *Molec. Endocrinol.* 4(8):1087–94; 1990. Hormone response elements are reviewed in Beato, *Cell* 56:335–44; 1989. A preferred promoter element in this regard is a serum response element, or SRE (see, e.g., Shaw et al., *Cell* 56:563–72, 1989). A preferred such reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:29094–101, 1994; Schenborn and Goiffin, *Promega Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. Assays of this type will detect compounds that directly block PAR4 ligand binding, as well as compounds that block processes in the cellular pathway subsequent to receptor-ligand binding. In the alternative, compounds or other samples can be tested for direct blocking of PAR4 binding using moieties tagged with a detectable label (e.g., $^{125}$I, biotin, horseradish peroxidase, FITC, and the like). Within assays of this type, the ability of a test sample to inhibit the activation PAR4 is indicative of inhibitory activity, which can be confirmed through secondary assays. The ability of a test sample to stimulate PAR4 activity may also be determined and confirmed through secondary assays.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991; and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

PAR4 polypeptides can also be used to prepare antibodies that specifically bind to PAR4 epitopes, peptides or polypeptides. The PAR4 polypeptide or a fragment thereof serves as an antigen (immunogen) to inoculate an animal and elicit an immune response. Suitable antigens would be the PAR4 polypeptide encoded by SEQ ID NO:2 from amino acid number G18 to amino acid number R78, or from amino acid number G48 to amino acid number R78, or from amino acid number C54 to amino acid number R78. Alternatively, polypeptides corresponding to any PAR4 extracellular loop may be suitable antigens. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a PAR4 polypeptide or a fragment thereof. The immunogenicity of a PAR4 polypeptide or fragment may be increased through the use of an adjuvant, such as alum (aluminum hydroxide) or Freund's complete or incomplete adjuvant. Polypeptides useful for immunization also include fusion polypeptides, such as fusions of PAR4 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to PAR4 protein or peptide, and selection of antibody display libraries in phage or similar vectors (for instance, through use of immobilized or labeled PAR4 protein or peptide). Genes encoding polypeptides having potential PAR4 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the PAR4 sequences disclosed herein to identify proteins which bind to PAR4. These "binding proteins" which interact with PAR4 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as PAR4 "antagonists" to block PAR4 binding and signal transduction in vitro and in vivo. These anti-PAR4 binding proteins would be useful for inhibiting cellular responses to protease-activated PAR4.

Antibodies are determined to be specifically binding if: 1) they exhibit a threshold level of binding activity, and/or 2) they do not significantly cross-react with related polypeptide molecules. First, antibodies herein specifically bind if they bind to a PAR4 polypeptide, peptide or epitope with a binding affinity ($K_a$) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Second, antibodies are determined to specifically bind if they do not significantly cross-react with related polypeptides. Antibodies do not significantly cross-react with related polypeptide molecules, for example, if they detect PAR4 but not known related polypeptides using a standard Western blot analysis (Ausubel et al., ibid.). Examples of known related polypeptides are orthologs, proteins from the same species that are members of a protein family (e.g. PARs), PAR4 polypeptides, and non-human PAR4. Moreover, antibodies may be "screened against" known related polypeptides to isolate a population that specifically binds to the inventive polypeptides. For example, antibodies raised to PAR4 are adsorbed to related polypeptides adhered to insoluble matrix; antibodies specific to PAR4 will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43:1–98, 1988; *Monoclonal Antibodies: Principles and Practice*, Goding, J. W. (eds.), *Academic Press Ltd.*, 1996; Benjamin et al., *Ann. Rev. Immunol.* 2:67–101, 1984.

A variety of assays known to those skilled in the art can be utilized to detect antibodies which specifically bind to PAR4 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant PAR4 protein, polypeptide or fragment.

Antibodies to PAR4 may be used for tagging cells that express PAR4; for isolating PAR4 or PAR4 fragments by affinity purification; for diagnostic assays for determining circulating levels of PAR4 polypeptides or fragments; for detecting or quantitating soluble PAR4 as marker of underlying pathology or disease; in analytical methods employing FACS; for screening expression libraries; for generating anti-idiotypic antibodies; and as neutralizing antibodies or as antagonists to block PAR4 protease-activated activities in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to PAR4 or fragments thereof may be used in vitro to detect denatured PAR4 or fragments thereof in assays, for example, Western Blots or other assays known in the art.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/ anti-complementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, PAR4-cytokine fusion proteins or antibody-cytokine fusion proteins can be used for enhancing in vivo killing of target tissues (for example, blood and bone marrow cancers), if the PAR4 polypeptide or fragment, or the anti-PAR4 antibody, targets the hyperproliferative blood or bone marrow cell (see, generally, Hornick et al., *Blood* 89:4437–47, 1997). This reference described fusion proteins that enable targeting of a cytokine to a desired site of action, thereby providing an elevated local concentration of cytokine. Suitable PAR4 polypeptides or fragments or anti-PAR4 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the PAR4 polypeptide or anti-PAR4 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Polynucleotides encoding PAR4 polypeptides or fragments are useful within gene therapy applications where it is desired to increase or inhibit PAR4 activity. If a mammal has a mutated or absent PAR4 gene, the PAR4 gene can be introduced into the cells of the mammal. In one embodiment, a gene encoding a PAR4 polypeptide or fragment is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–28, 1989).

In another embodiment, a PAR4 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–17, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–67, 1992; Wu et al., *J. Biol. Chem.* 263:14621–24, 1988.

Antisense methodology can be used to inhibit PAR4 gene or fragment transcription, such as to inhibit cell proliferation in vivo. Polynucleotides that are complementary to a segment of a PAR4-encoding polynucleotide (e.g., a polynucleotide as set froth in SEQ ID NO:1) are designed to bind to PAR4-encoding mRNA and to inhibit translation of such mRNA. Such antisense polynucleotides are used to inhibit expression of PAR4 polypeptide-encoding genes in cell culture or in a subject.

The present invention also provides reagents which will find use in diagnostic applications. For example, the PAR4 gene, a probe comprising PAR4 DNA or RNA or a subsequence thereof can be used to determine if the PAR4 gene is present on a particular chromosome, or if a mutation has occurred. Detectable chromosomal aberrations at the PAR4 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et al., ibid.; Marian, *Chest* 108:255–65, 1995).

Transgenic mice, engineered to express the PAR4 gene, and mice that exhibit a complete absence of PAR4 gene function, referred to as "knockout mice" (Snouwaert et al., *Science* 257:1083, 1992), may also be generated (Lowell et al., *Nature* 366:740–42, 1993). These mice may be employed to study the PAR4 gene and the protein encoded thereby in an in vivo system.

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, Md. http://www.ncbi.nlm.nih.gov), and can be searched with a gene sequence of interest for the mapping data contained within these short genomic landmark STS sequences.

For pharmaceutical use, PAR4 fragments that stimulate or inhibit PAR4 activation are formulated for parenteral, particularly intravenous or subcutaneous, delivery according to conventional methods. Intravenous administration will be by bolus injection or infusion over a typical period of one to several hours. In general, pharmaceutical formulations will include a PAR4 fragment in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5–20 µg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of a PAR4 fragment is an amount sufficient to produce a clinically significant change in unwanted cellular activation or responsiveness.

The invention is further illustrated by the following non-limiting examples.

EXAMPLES

Example 1

PAR4 Polynucleotide and Polypeptide

A search of various databases was conducted to identify ESTs with homology to the three known protease-activated receptors (PAR1, PAR2 and PAR3). One EST sequence was identified that showed homology to the three protease-activated receptors in the fourth transmembrane domain. More particularly, the deduced amino acid sequence corresponding to this EST nucleotide sequence shared 34% identity with PAR2 in the transmembrane region.

A size-selected lymphoma Daudi cell line cDNA library containing inserts greater than about 2 kb was then screened, using a 600 bp DNA probe derived from the EST sequence. The DNA probe, corresponding to nucleotides 818–1391 of SEQ ID NO:1, was prepared by PCR amplification using Daudi cell cDNA as a template. Screening of the cDNA library was carried out by standard filter hybridization techniques with radioactive DNA probes labeled by random priming (Prime-it kit, Stratagene, La Jolla, Calif.). cDNA inserts were sequenced on both strands by the dideoxy chain termination method (F. Sanger et al., *Proc. Natl. Acad. Sci. USA* 74:5463–67, 1977) using the Sequenase Kit from US Biochemicals (Cleveland, Ohio).

A full-length cDNA clone (4.9 kb) was identified, sequenced on both strands, and designated as protease-activated receptor 4 (PAR4). The DNA sequence revealed a 5'-untranslated region (nucleotides 1–175 of SEQ ID NO:1), an open reading frame encoding a 385 amino acid protein (nucleotides 176–1330 of SEQ ID NO:1), and a long GC-rich 3'-untranslated region containing several polyadenylation signals and a poly(A) tail (nucleotides 1331–4895 of SEQ ID NO:1).

A hydropathy plot of the amino-acid sequence of PAR4 revealed that the receptor was a member of the seven transmembrane domain receptor family, as illustrated in FIG. 1. A hydrophobic signal sequence with a potential signal peptidase cleavage site was present at S17/G18. A putative cleavage site for protease activation at R47/G48 was also present within the extracellular amino terminus. Alignment of the PAR4 amino acid sequence with the three other known protease-activated receptors indicated that PAR4 was a member of the protease-activated receptor family, with about 33% overall amino acid sequence identity with PAR1, PAR2, or PAR3. However, the extracellular amino terminus and intracellular carboxy terminus of PAR4 have little or no amino acid sequence similarity to the corresponding regions in the other family members. The protease cleavage site in PAR4 differs substantially from that in PAR1 and PAR3. In the second extracellular loop, PAR4 has only three amino acids (CHD) that match the sequence of ITTCHDV (SEQ ID NO:4) that is conserved in PAR1, PAR2, and PAR3.

Example 2

Activation of PAR4 by Thrombin and Trypsin

The similarity in sequence between PAR4 and the other protease-activated receptors suggested that PAR4 should be activated by an arginine-specific serine protease. For comparative purposes, PAR1 protein was prepared. Briefly, the cDNA coding for PAR1 was isolated from a placental cDNA library by PCR. The PAR1 DNA sequence obtained was essentially identical to that previously reported, except for nucleotides 711–712 (CG→GC) and nucleotides 1091–1092 (CG→GC). These differences resulted in a change of V→L at amino acid residue 238 and a change of S→C at amino acid residue 364, respectively. These amino acid changes were confirmed by sequence analysis of the corresponding regions in the genomic DNA coding for PAR1.

COS cells were transiently transfected with PAR4 cDNA, and examined for responses to thrombin and trypsin. Briefly, for the phosphoinositide hydrolysis assay, COS-7 cells were grown in Dulbecco's modified Eagle's medium (DMEM; Gibco/BRL, Gaithersburg, Md.) with 10% fetal bovine serum (FBS). Cells were plated at $3.5 \times 10^5$/35-mm plate one day before transfection. Two µg of DNA were transfected using 12 µl of lipofectAMINE (Gibco/BRL) for 5 h. The cells were incubated overnight in DMEM with 10% FBS, and then split into triplicate 35-mm wells. Forty-eight hours after transfection, the cells were loaded with 2 µCi/ml [$^3$H]myo-inositol (Amersham, Arlington Heights, Ill.) in serum-free DMEM and incubated overnight at 37° C. Cells were washed and treated with 20 mM LiCl in DMEM, with or without protease or peptide activators added at various concentrations. Cells were then incubated for 2 h at 37° C. and extracted with 750 µl of 20 mM formic acid for 30 min on ice. The inositol mono-, bis-, and trisphosphates were purified through a one ml AG 1-X8 anion-exchange resin (Bio-Rad, Hercules, Calif.) (T. Nanevicz et al., *J. Biol. Chem.* 271:702–06, 1996), and quantitated by scintillation counting. In each hydrolysis assay, surface expression levels of receptors were determined in triplicate in parallel cultures.

The PAR4-transfected COS cells did respond to thrombin or trypsin addition (100 nM), resulting in phosphatidylinositol 4,5 diphosphate hydrolysis. This response was comparable to the thrombin-stimulated activation of PAR1. Gamma-thrombin that lacks a fibrinogen-binding exosite (T. J. Rydel et al., *J. Biol. Chem.* 269:22000–06, 1994)(Enzyme Research Laboratories, Inc., South Bend, Ind.) was as effective as α-thrombin in the activation of PAR4. This is in contrast to the activation of PAR1 and PAR3, where γ-thrombin is much less potent than α-thrombin. This difference in activation is probably due to the presence of an additional thrombin binding site within the amino terminal region of PAR1 and PAR3. The thrombin-stimulated phosphoinositide hydrolysis with PAR4 was dose-dependent, with a half-maximal concentration (EC50) for thrombin and trypsin of 5 nM. This dose level was much higher than that for PAR1 and PAR3 (about 0.2 nM).

Other arginine/lysine-specific serine proteases, including factor VIIa, IXa, XIa, urokinase, or plasmin, had little or no activity against PAR4. Small effects, however, were observed with factor Xa at high concentrations (100 nM). Chymotrypsin and elastase failed to activate PAR4.

Site-directed mutagenesis was employed to evaluate the importance of the putative cleavage site at R47/G48 in PAR4 activation. A cDNA encoding PAR4 with a single amino acid substitution of Ala for Arg at residue 47 was transiently expressed in COS cells. The putative cleavage site mutant (R47A) failed to respond to either thrombin or trypsin. In contrast, a mutation of Arg at residue 68 in the extracellular amino-terminal region (R68A) had no effect on PAR4 activation by thrombin or trypsin in the phosphatidylinositol 4,5 diphosphate hydrolysis assay. Thus, the putative protease cleavage site of R47/G48 in PAR4 was critical for receptor activation.

Example 3

Epitope-tagged PAR4 Assay

Surface expression of wild-type and mutant PAR4 polypeptide was determined using specific binding of monoclonal antibody M1 (Eastman Kodak Company, Scientific Imaging Systems, New Haven Conn.) directed at a FLAG epitope inserted at PAR4's amino terminus. The cDNA employed for the epitope-tagged PAR4 assay was prepared analogous to FLAG-epitope-tagged PAR1 with an amino terminus sequence of MDSKGSSQKGSRLLLLLVVSN LLLCQGVVS↓DYKDDDDKLE-GG (SEQ ID NO:5). This sequence represents the bovine prolactin signal peptide, the putative signal peptidase site (↓), the FLAG epitope DYKD-DDDK (SEQ ID NO:6), and a junction of LE providing a XhoI cloning site (H. Ishihara et al., *Nature* 386:502–06, 1997). This sequence (SEQ ID NO:5) was fused to G18 in PAR4. Receptor cDNAs were subcloned into the mammalian expression vector pZP-7. Receptor expression on the COS cell surface was measured as specific binding of monoclonal antibody M1 to the FLAG epitope at the amino terminus of PAR4 (see K. Ishii et al., *J. Biol. Chem.* 268:9780–86, 1993).

Briefly, transfected COS cells were split into 24-well plates (Falcon, Becton Dickinson Labware Company, Lincoln Park, N.J.) at $1\times10^5$ cells/well. One day later, cells were washed with Dulbecco's modified Eagle's medium (DMEM) containing 10 mM Hepes (pH 7.4), 50 mM Tris-HCl, and 1 mM $CaCl_2$. Cells were thereafter exposed to various proteases for selected times at 37° C., then fixed with 4% paraformaldehyde in 150 mM sodium chloride, 10 mM sodium phosphate (pH 7.0), 1 mM calcium chloride (phosphate-buffered saline, PBS), 50 mM Tris-HCl for 5 min on ice. Plates were washed twice with PBS, and then incubated with primary monoclonal anti-FLAG antibody M1 (0.5 µg/ml) in DMEM/Hepes/Tris-HCl/$CaCl_2$/bovine serum albumin (BSA, 1 mg/ml) for 1 h at room temperature. Plates were washed with PBS and incubated with horseradish peroxidase (HRP)-conjugated goat-anti-mouse second antibody (Bio-Rad; 1:1,000 dilution) in DMEM/Hepes/Tris-HCl/$CaCl_2$/BSA for 30 min at room temperature. After additional washing with PBS, plates were developed with the HRP chromogenic substrate 2,2'-azino-di[3-ethyl-benzthiazoline-6-sulfonic acid] (Bio-Rad). $OD_{415}$ was read after 5–10 min. Antibody binding data are expressed as specific binding (total minus nonspecific binding, with nonspecific being defined as the level of binding seen on untransfected control COS cells).

Example 4

Protease Receptor Activating Peptide

The protease-activated receptor family has been shown to be activated by a peptide derived from the amino terminus of the receptor protein. Accordingly, a hexapeptide (GYPGQV; SEQ ID NO:7), corresponding to the amino terminus of PAR4 that is unmasked following cleavage at R47/G48, was tested for its ability to stimulate COS cells expressing PAR4. This peptide readily activated both wild-type and mutant PAR4 (R47A) at 500 µM, whereas thrombin and trypsin only activate the wild-type PAR4. COS cells with no transfected DNA failed to respond to the activating peptide under the same conditions. The maximal response of cells expressing PAR4 to the activating peptide was comparable to the maximal response to thrombin or trypsin. The activating peptide (SFLLRN; SEQ ID NO:8) from PAR1 showed no activity toward PAR4 when tested at a concentration effective for PAR1 activation. The EC50 of PAR4 activating peptide was about 100 µM, which is substantially higher than that of the activating peptide for PAR1. The high EC50 for the activating peptide for PAR4, as compared to thrombin or trypsin, clearly reflects the difference between a built-in tethered ligand and a ligand in free solution.

Example 5

Potential Intracellular Phosphorylation Sites

Since the termination of the signaling of PAR4 may occur by phosphorylation (analogous to the β-adrenergic receptor; see K. Ishii et al., *J. Biol. Chem.* 269:1125–1130, 1994), the intracellular regions of PAR4 were examined for potential phosphorylation sites. A serine residue is present in the third intracellular loop of PAR4 that could be phosphorylated by protein kinase C, while another serine residue is present in the carboxy terminal region that could be phosphorylated by casein kinase II (FIG. 1). Accordingly, the termination of PAR4 signaling may be similar to that for other seven transmembrane receptors.

Example 6

Tissue Distribution of PAR4

The tissue distribution of PAR4 was examined by Northern blot analysis. Briefly, three human multiple-tissue blots with 2 µg mRNA in each lane (ClonTech, Palo Alto, Calif.) were hybridized with a [$^{32}$P]-labeled 166 bp PCR product generated from human lymph node cDNA with PCR4 specific primers, 5'-TGGCACTGCCCCTGACACTGCA-3' (SEQ ID NO:9) and 5'-CCCGTAGCACAGCAGCATGG-3' (SEQ ID NO:10). Hybridization to human β-actin mRNA was used as a control for variation in abundance. The blots were hybridized overnight in ExpressHyb (ClonTech) and washed at 50° C. in 0.1×SSC, 0.1% SDS, followed by exposure to X-ray film. Northern blot analysis of mRNA from 23 different tissues showed that the PAR4 gene was expressed in most of the tissues tested, with especially high levels in lung, pancreas, thyroid, testis, and small intestine. Moderate expression was also detected in prostate, placenta, skeletal muscle, lymph node, adrenal gland, uterus, and colon. No PAR4 expression was detected in brain, kidney, spinal cord, and peripheral blood leukocytes. The PAR4 mRNA was also detected in human platelets by RT-PCR, although the expression of PAR4 was much less than that of PAR1.

Example 7

Chromosomal Localization of PAR4

The Human Genetic Mutant Cell Repository Human/Rodent Somatic Cell Hybrid Mapping Panel Number 2 (National Institute of General Medical Sciences, Coriell Institute of Medical Research) was used with PCR amplification to identify the somatic hybrid that contained the human PAR4 gene (R. E. Kuestner et al., *Mol. Pharm.* 46:246–55, 1994). PAR4 specific oligonucleotide primers (sense, 5'-GGTGCCCGCCCTCTATGG-3' (SEQ ID NO:11), and anti-sense, 5'-TCGCGAGGTTCATCAGCA-3' (SEQ ID NO:12)) were used for the PCR amplification. Subchromosomal mapping of the PAR4 gene was carried out using the commercially available version of the Stanford G3 Radiation Hybrid Mapping Panel (Research Genetics, Inc., Huntsville, Ala.). The Stanford G3 RH Panel contains PCR-amplifiable DNAs from each of 83 radiation hybrid clones of the whole human genome, plus two control DNAs (the RM donor and the A3 recipient). A publicly available WWW server (http://shgc-www.stanford.edu) permitted chromosomal localization of markers. The PCR amplification with the same set of primers was set up in a 96-well microtiter plate and used in a RoboCycler Gradient 96 thermal cycler (Stratagene). The PCR products were separated by electrophoresis on a 2% agarose gel.

The PAR4 gene was mapped to chromosomal location 19p12. This location was different from that of the PAR1 and PAR2 genes, which are located within approximately 100 kb of each other at chromosome 5q13. The location of the two latter genes suggested that they arose from a gene duplication event (M. Kahn et al., *Mol. Med.* 2:349–57, 1996). At present, the localization of PAR3 is unknown. Additional members of the PAR family probably exist that have evolved through a combination of retroposition and gene duplication (W. C. Probst et al., *DNA Cell Biol.* 11:1–20, 1997).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide molecule that encodes a polypeptide comprising amino acid residues 48 to 78 of SEQ ID NO:2.

2. The isolated polynucleotide molecule of claim 1, wherein the polynucleotide molecule comprises nucleotides 317 to 409 of SEQ ID NO:1.

3. A composition comprising the isolated polynucleotide molecule of claim 1.

4. The isolated polynucleotide molecule of claim 1, wherein the polynucleotide molecule is a DNA molecule.

5. A vector, comprising the isolated polynucleotide molecule of claim 1.

6. The isolated polynucleotide molecule of claim 1, wherein the polynucleotide molecule encodes a polypeptide comprising amino acid residues 18 to 78 of SEQ ID NO:2.

7. The isolated polynucleotide molecule of claim 6, wherein the polynucleotide molecule comprises nucleotides 227 to 409 of SEQ ID NO:1.

8. The isolated polynucleotide molecule of claim 1, wherein the polynucleotide molecule encodes a polypeptide comprising amino acid residues 18 to 385 of SE ID NO:2.

9. The isolated polynucleotide molecule of claim 8, wherein the polynucleotide molecule comprises nucleotides 227 to 1330 of SEQ ID NO:1.

10. The isolated polynucleotide molecule of claim 1, wherein the polynucleotide molecule encodes a polypeptide comprising amino acid residues 1 to 385 of SEQ ID NO:2.

11. The isolated polynucleotide molecule of claim 10, wherein the polynucleotide molecule comprises nucleotides 176 to 1330 of SEQ ID NO:1.

12. An isolated polynucleotide molecule that encodes the amino acid sequence of SEQ ID NO:7.

13. An isolated polynucleotide molecule comprising a nucleotide sequence that is complementary to the nucleotide sequence of SEQ ID NO:1.

14. An expression vector, comprising a polynucleotide molecule that encodes a polypeptide comprising amino acid residues 18 to 78 of SEQ ID NO:2, a transcription promoter, and a transcription terminator, wherein the promoter is operably linked with the polynucleotide molecule, and wherein the polynucleotide molecule is operably linked with the transcription terminator.

15. The expression vector of claim 14, wherein the polynucleotide molecule encodes a polypeptide comprising amino acid residues 18 to 385 of SEQ ID NO:2.

16. A host cell comprising the expression vector of claim 14, wherein the host cell is selected from the group consisting of bacterium, yeast cell, fungal cell, insect cell, mammalian cell, and plant cell.

17. The host cell of claim 16, wherein the host cell is a bacterial host cell, which is either an *E. coli* cell or a *Bacillus* cell.

18. The host cell of claim 16, wherein the host cell is a fungal cell, which is either a *Saccharomyces* cell or a *Pichia* cell.

19. The host cell of claim 16, wherein the host cell is a mammalian cell.

20. The host cell of claim 19, wherein the mammalian cell is a human cell.

21. A method of using the expression vector of claim 14 to produce a protease activated receptor-4 polypeptide, the method comprising the act of culturing host cells that comprise the expression vector and that produce a protease activated receptor-4 polypeptide.

22. The method of claim 21, further comprising the act of isolating the protease activated receptor-4 from the cultured host cells.

23. A virus, comprising the expression vector of claim 14.

* * * * *

UNITED STATES PATENT AND TRADEMARK OFFICE
CERTIFICATE OF CORRECTION

PATENT NO. : 7,122,342 B1 Page 1 of 1
APPLICATION NO. : 09/371333
DATED : October 17, 2006
INVENTOR(S) : Wen-feng Xu et al.

It is certified that error appears in the above-identified patent and that said Letters Patent is hereby corrected as shown below:

Column 3, line 67, "ATGGTTAGCTT" should be changed to "ATGGCTTAGCTT".

Column 18, line 1, "Saccharonyces" should be changed to "Saccharomyces".

Signed and Sealed this

Twenty-fifth Day of November, 2008

JON W. DUDAS
*Director of the United States Patent and Trademark Office*

SEQUENCE LISTING

<160> NUMBER OF SEQ ID NOS: 21

<210> SEQ ID NO 1
<211> LENGTH: 4895
<212> TYPE: DNA
<213> ORGANISM: Homo sapiens
<220> FEATURE:
<221> NAME/KEY: CDS
<222> LOCATION: (176)...(1330)

<400> SEQUENCE: 1

```
ctcccacggg ctggctggca agcggccctg gtgggtctgc gggggcaggg gcagccttcc      60
tggtttatct ccaccggcgc gatctgctcg tccgcctcgg ctccagaagc tggggctcag     120
ggtccggcga ggcaggaagc ctgaggccac agcccagagc agcctgagtg cagtc atg      178
                                                                 Met
                                                                   1 tgg ggg cga ctg ctc ctg tgg ccc ctg gtg ctg ggg ttc agc ctg tct      226
Trp Gly Arg Leu Leu Leu Trp Pro Leu Val Leu Gly Phe Ser Leu Ser
            5                   10                  15 ggc ggc acc cag acc ccc agc gtc tac gac gag agc ggg agc acc gga      274
Gly Gly Thr Gln Thr Pro Ser Val Tyr Asp Glu Ser Gly Ser Thr Gly
         20                  25                  30 ggt ggt gat gac agc acg ccc tca atc ctg cct gcc ccc cgc ggc tac      322
Gly Gly Asp Asp Ser Thr Pro Ser Ile Leu Pro Ala Pro Arg Gly Tyr
 35                  40                  45 cca ggc caa gtc tgt gcc aat gac agt gac acc ctg gag ctc ccg gac      370
Pro Gly Gln Val Cys Ala Asn Asp Ser Asp Thr Leu Glu Leu Pro Asp
 50                  55                  60                  65 agc tca cgg gca ctg ctt ctg ggc tgg gtg ccc acc agg ctg gtg ccc      418
Ser Ser Arg Ala Leu Leu Leu Gly Trp Val Pro Thr Arg Leu Val Pro
                 70                  75                  80 gcc ctc tat ggg ctg gtc ctg gtg gtg ggg ctg ccg gcc aat ggg ctg      466
Ala Leu Tyr Gly Leu Val Leu Val Val Gly Leu Pro Ala Asn Gly Leu
             85                  90                  95 gcg ctg tgg gtg ctg gcc acg cag gca cct cgg ctg ccc tcc acc atg      514
Ala Leu Trp Val Leu Ala Thr Gln Ala Pro Arg Leu Pro Ser Thr Met
        100                 105                 110 ctg ctg atg aac ctc gcg act gct gac ctc ctg ctg gcc ctg gcg ctg      562
Leu Leu Met Asn Leu Ala Thr Ala Asp Leu Leu Leu Ala Leu Ala Leu
    115                 120                 125 ccc ccg cgg atc gcc tac cac ctg cgt ggc cag cgc tgg ccc ttc ggg      610
Pro Pro Arg Ile Ala Tyr His Leu Arg Gly Gln Arg Trp Pro Phe Gly
130                 135                 140                 145 gag gcc gcc tgc cgc ctg gcc acg gcc gca ctc tat ggt cac atg tat      658
Glu Ala Ala Cys Arg Leu Ala Thr Ala Ala Leu Tyr Gly His Met Tyr
                150                 155                 160 ggc tca gtg ctg ctg ctg gcc gcc gtc agc ctg gat cgc tac ctg gcc      706
Gly Ser Val Leu Leu Leu Ala Ala Val Ser Leu Asp Arg Tyr Leu Ala
            165                 170                 175 ctg gtg cac ccg ctg cgg gcc cgc gcc ctg cgt ggc cgg cgc ctg gcc      754
Leu Val His Pro Leu Arg Ala Arg Ala Leu Arg Gly Arg Arg Leu Ala
        180                 185                 190 ctt gga ctc tgc atg gct gct tgg ctc atg gcg gcc gcc ctg gca ctg      802
Leu Gly Leu Cys Met Ala Ala Trp Leu Met Ala Ala Ala Leu Ala Leu
    195                 200                 205
```

| | |
|---|---|
| ccc ctg aca ctg cag cgg cag acc ttc cgg ctg gcg cgc tcc gat cgc<br>Pro Leu Thr Leu Gln Arg Gln Thr Phe Arg Leu Ala Arg Ser Asp Arg<br>210                                        215                                220                                225 | 850 |
| gtg ctc tgc cat gac gcg ctg ccc ctg gac gca cag gcc tcc cac tgg<br>Val Leu Cys His Asp Ala Leu Pro Leu Asp Ala Gln Ala Ser His Trp<br>                              230                                235                                240 | 898 |
| caa ccg gcc ttc acc tgc ctg gcg ctg ttg ggc tgt ttc ctg ccc ctg<br>Gln Pro Ala Phe Thr Cys Leu Ala Leu Leu Gly Cys Phe Leu Pro Leu<br>              245                                250                                255 | 946 |
| ctg gcc atg ctg ctg tgc tac ggg gcc acc ctg cac acg ctg gcg gcc<br>Leu Ala Met Leu Leu Cys Tyr Gly Ala Thr Leu His Thr Leu Ala Ala<br>260                                        265                                270 | 994 |
| agc ggc cgg cgc tac ggc cac gcg ctg agg ctg acc gca gtg gtg ctg<br>Ser Gly Arg Arg Tyr Gly His Ala Leu Arg Leu Thr Ala Val Val Leu<br>              275                                280                                285 | 1042 |
| gcc tcc gcc gtg gcc ttc ttc gtg ccc agc aac ctg ctg ctg ctg<br>Ala Ser Ala Val Ala Phe Phe Val Pro Ser Asn Leu Leu Leu Leu Leu<br>290                                        295                                300                                305 | 1090 |
| cat tac tcg gac ccg agc ccc agc gcc tgg ggc aac ctc tat ggt gcc<br>His Tyr Ser Asp Pro Ser Pro Ser Ala Trp Gly Asn Leu Tyr Gly Ala<br>                              310                                315                                320 | 1138 |
| tac gtg ccc agc ctg gcg ctg agc acc ctc aac agc tgc gtg gat ccc<br>Tyr Val Pro Ser Leu Ala Leu Ser Thr Leu Asn Ser Cys Val Asp Pro<br>              325                                330                                335 | 1186 |
| ttc atc tac tac tac gtg tcg gcc gag ttc agg gac aag gtg cgg gca<br>Phe Ile Tyr Tyr Tyr Val Ser Ala Glu Phe Arg Asp Lys Val Arg Ala<br>                              340                                345                                350 | 1234 |
| ggg ctc ttc caa cgg tcg ccg ggg gac acc gtg gcc tcc aag gcc tct<br>Gly Leu Phe Gln Arg Ser Pro Gly Asp Thr Val Ala Ser Lys Ala Ser<br>355                                        360                                365 | 1282 |
| gcg gaa ggg ggc agc cgg ggc atg ggc acc cac tcc tct ttg ctc cag<br>Ala Glu Gly Gly Ser Arg Gly Met Gly Thr His Ser Ser Leu Leu Gln<br>370                                        375                                380                                385 | 1330 |
| tgacacaaag tggggaaggc tgtactgggt cgaacagggt cccttccccc acttcacgtc | 1390 |
| cttcctggga cctcagaatg tgaccttatt tggaaatagg gttgttacaa ctgtcactag | 1450 |
| cggaggtcac tttggagaag ggtgggcctt acatccagtg tgggtggtgt cctcataaga | 1510 |
| taaggagagg ccaggcctgg tggctcacgc ctgtaatccc agcactttaa gaggccaagg | 1570 |
| cggatggatc acttgagccc aggagttcaa caccagcctg agcaacatgg taaaacccca | 1630 |
| tctctaccaa aaatacaaaa attagctggg cttggtggct ggcgcctgta atcccagcta | 1690 |
| ctcaggagac tgaggcagaa ggatcgcttg aacctgggag gcagaggttg cagtgagccg | 1750 |
| agattgcgcc actggactcc agcctgcgtg acagagagcc tgtctctaaa ttaattaatt | 1810 |
| aattaattta attcaatttt aaaaagacga aaagtgacgg ccaggtgcag tggctcacgc | 1870 |
| ctataatctc agcactctgg gaggccaaga tggaggattg cttgaagcca ggagtttggg | 1930 |
| accagcctgg gcaacatagg gggatcccat ctctacacac aaaaaaattt tttaatgaac | 1990 |
| caggcattgt ggcatgcgcc tatagtccca gccactcaag aggcacaggc gggaggatca | 2050 |
| cttgagcctg ggaggttgtg gttgcagtga gctatgattg taccactgca ctccagcctg | 2110 |
| ggcaacagag caagaccttg tctcaaaaat aaacaaacta aaattaaaaa agaagacga | 2170 |
| gagatagtgg gtgtggtggc tcacacctgc aatcccagca ctttggaagg ccgaggtggg | 2230 |
| cagatcatct gaggccagga gttcaagacc agcctggcta acatggtgaa atcctatctc | 2290 |
| taccaaaaat acaaaaatta gccaggcgtg gtggtgggca cctgtactgg ggaggtgccc | 2350 |

```
acccagctac tggggaggct gagtcaggag aatcgcttga acctgggagg cggaggttgc    2410
ggtcagctga gatggtgcca ctgcactcca gcctgggcga aagagcgact ctgtctccaa    2470
aaaaaagaga agaggagagg acacagagac acacagagaa gaaagccatg tggcggcaga    2530
ggcagagatg ggagtgatgc ggacggacac aaactaaggg atgccacgat gccaagcaca    2590
gccaacagcc accagcagcc aggagacagg cctgggacgg gctctccctc acagcctcca    2650
gagggaacca gccctgccac caccttgacc ctggacttct ggcctgcaga actgtgagac    2710
aataaactct cattgtttta agctgcctgg catgtggcac tttgtcaggg cagcccagga    2770
atctgaaaca ggatcaaact ctgcttcctg ggccctgcca gcatctctgg ctcggctttc    2830
tgggctggat gcagcccacg acgcactggt gtctgagatg gggctggagc tggggctggg    2890
gctgcattcc ctggagactc actgcaagtt cctgcccagg aggctgaggg caccccatcc    2950
tcagtgccca atgctgtggc cccaccaggc ccagagcctg gttggccatt ctcatgccca    3010
ccagcttctg gctttgggat gtctcttgag caaccagaat agcaccccca actctgctcc    3070
ccaaaaccca tcactagcac ggctcagcct cctgctatcc cctgactgct ggggaccctc    3130
gccttccctc ctctcacctg caggctgatc cttcttttca ctttctgtca atgtcaccag    3190
ggataaggtg ggacaatggg gggtgggggt ggacagtgtg tgctgggggg ttcgggtgct    3250
gcagacctgg aactcccttc tgccaggatg ttggcagccg gttgtaagcc ttgcacggga    3310
cagaccacac ccaccgcaac ctcatcccct cagcactaac cacatccact ctcaaccccg    3370 tcccccttcgc actgaccaca cccacccccgt tcggccccgc ccccgcact gaacactccc    3430 gccctcaacc ccgcaccctc cgcactcacc tccccctcgc cgctcgaccc cgccctcacc    3490
acactgacca ccctcaaccc attgcgccca gtccccacca cagtgaccac accctcactg    3550
gctcggccct gcccccagta tactgaccat tccccagcca cttcccttcc gcacttacca    3610
ctcccccagc cacgcccctc cccgctgacc gctcctccag ccccgcctcc cccgtacagg    3670
cagagcgccc gcccacctct atgctgcgtt ctcctgactt tacgttggcc cctcctctgc    3730
caagccccca ggggagccct ccctggcgtc cgagggtggg agtcggggtg tggcaggccg    3790
cggtgggggg cggcagtggc tccgcgcact cacccgggcc ccgggcaggg gcgcgctcca    3850
cttcgttgca cgcgggtccg gcgcacagtt cccgggcgag tgggctgtgc gtgctgacgt    3910
tgtagaagcg agtggcctcg aaggctacgg gacgagggtg gcgggtgacc aagtgcaggc    3970
gcgacgggtc agggaccggg ccgggccggg ggtgcgggcg cgcgggccta ccgggttcgt    4030
agtagtcgta cacggagact ggcagcgccg acgtcctgcc caccacgcac tcccggagag    4090
cacggaaccg cacgcacgtc aggcaccggc tggggatctg tggggcagcg gcgggcgcag    4150
gctcgacccg ggccaggagg cccggggcgc tgagctcagg cccagaactg gctgatttca    4210
gggataccca ggacgcgtga aacacagaag aaacgtgatc ccattttctt ttttctttt    4270 acttttcttt tttttttttt ttcctgagac agagtctcgc gctgttgccc aggctggagt    4330
gcagtggcgt gatctcggct cactgcaagc tcggcctcct gggttcaaat gattctcctg    4390
cctcagcctc ccaagtagct gggataacag gcgcccacca ccgcaccctg ctaatttttt    4450 gtattttga tcaagacgga gtttcaccat gttggccagg ctggtctcca actcctgccc    4510
tcaagtgatc cgcctcggtc ccatttttta ttctttgggt ccttccatcc cactgggaaa    4570
acgtctcagg tggcctctga aacaccactc cttttgtgt gtgtgcacgc atggctgagc    4630
atgtgtgggt gggagtcagc acattcacga tactgtgcaa tcatcacctc tgtctagtta    4690
caggacggtt tcttctcccc caaagaaac cccatcgcca tcagcactca ctccccactc    4750
```

-continued

```
cccagcccc tggcaaccac aaatctttcc aactctacgg atttgcctgt tctgggcatt    4810
tcatgtcaat ggaatcatgt actctgtgaa aaaaaaaaaa aaaaaaaaaa aaaaaaaaaa    4870
aaaaaaaaaa aaaaaaaaaa aaaaa                                         4895
```

<210> SEQ ID NO 2
<211> LENGTH: 385
<212> TYPE: PRT
<213> ORGANISM: Homo sapiens

<400> SEQUENCE: 2

```
Met Trp Gly Arg Leu Leu Trp Pro Leu Val Leu Gly Phe Ser Leu
 1               5                  10                  15

Ser Gly Gly Thr Gln Thr Pro Ser Val Tyr Asp Glu Ser Gly Ser Thr
                20                  25                  30

Gly Gly Gly Asp Asp Ser Thr Pro Ser Ile Leu Pro Ala Pro Arg Gly
            35                  40                  45

Tyr Pro Gly Gln Val Cys Ala Asn Asp Ser Asp Thr Leu Glu Leu Pro
        50                  55                  60

Asp Ser Ser Arg Ala Leu Leu Leu Gly Trp Val Pro Thr Arg Leu Val
 65                  70                  75                  80

Pro Ala Leu Tyr Gly Leu Val Leu Val Gly Leu Pro Ala Asn Gly
                85                  90                  95

Leu Ala Leu Trp Val Leu Ala Thr Gln Ala Pro Arg Leu Pro Ser Thr
                100                 105                 110

Met Leu Leu Met Asn Leu Ala Thr Ala Asp Leu Leu Leu Ala Leu Ala
                115                 120                 125

Leu Pro Pro Arg Ile Ala Tyr His Leu Arg Gly Gln Arg Trp Pro Phe
            130                 135                 140

Gly Glu Ala Ala Cys Arg Leu Ala Thr Ala Ala Leu Tyr Gly His Met
145                 150                 155                 160

Tyr Gly Ser Val Leu Leu Leu Ala Ala Val Ser Leu Asp Arg Tyr Leu
                165                 170                 175

Ala Leu Val His Pro Leu Arg Ala Arg Ala Leu Arg Gly Arg Arg Leu
                180                 185                 190

Ala Leu Gly Leu Cys Met Ala Ala Trp Leu Met Ala Ala Ala Leu Ala
            195                 200                 205

Leu Pro Leu Thr Leu Gln Arg Gln Thr Phe Arg Leu Ala Arg Ser Asp
        210                 215                 220

Arg Val Leu Cys His Asp Ala Leu Pro Leu Asp Ala Gln Ala Ser His
225                 230                 235                 240

Trp Gln Pro Ala Phe Thr Cys Leu Ala Leu Leu Gly Cys Phe Leu Pro
                245                 250                 255

Leu Leu Ala Met Leu Leu Cys Tyr Gly Ala Thr Leu His Thr Leu Ala
                260                 265                 270

Ala Ser Gly Arg Arg Tyr Gly His Ala Leu Arg Leu Thr Ala Val Val
            275                 280                 285

Leu Ala Ser Ala Val Ala Phe Val Pro Ser Asn Leu Leu Leu Leu
        290                 295                 300

Leu His Tyr Ser Asp Pro Ser Pro Ser Ala Trp Gly Asn Leu Tyr Gly
305                 310                 315                 320

Ala Tyr Val Pro Ser Leu Ala Leu Ser Thr Leu Asn Ser Cys Val Asp
                325                 330                 335

Pro Phe Ile Tyr Tyr Tyr Val Ser Ala Glu Phe Arg Asp Lys Val Arg
```

```
                    340             345             350
Ala Gly Leu Phe Gln Arg Ser Pro Gly Asp Thr Val Ala Ser Lys Ala
        355             360             365

Ser Ala Glu Gly Gly Ser Arg Gly Met Gly Thr His Ser Ser Leu Leu
    370             375             380

Gln
385

<210> SEQ ID NO 3
<211> LENGTH: 1155
<212> TYPE: DNA
<213> ORGANISM: Artificial Sequence
<220> FEATURE:
<223> OTHER INFORMATION: This degenerate nucleotide sequence encodes the
      amino acid sequence of SEQ ID NO:2.
<221> NAME/KEY: variation
<222> LOCATION: (1)...(1155)
<223> OTHER INFORMATION: N is any nucleotide.

<400> SEQUENCE: 3
atgtggggnm gnytnytnyt ntggccnytn gtnytnggnt tywsnytnws nggnggnacn     60
caracnccnw sngtntayga ygarwsnggn wsnacnggng gnggngayga ywsnacnccn    120
wsnathytnc cngcnccnmg nggntayccn ggncargtnt gygcnaayga ywsngayacn    180
ytngarytnc cngaywsnws nmgngcnytn ytnytnggnt gggtnccnac nmgnytngtn    240
ccngcnytnt ayggnytngt nytngtngtn ggnytnccng cnaayggnyt ngcnytntgg    300
gtnytngcna cncargcncc nmgnytnccn wsnacnatgy tnytnatgaa yytngcnacn    360
gcngayytny tnytngcnyt ngcnytnccn ccnmgnathg cntaycayyt nmgnggncar    420
mgntggccnt tyggngargc ngcntgymgn ytngcnacng cngcnytnta yggncayatg    480
tayggnwsng tnytnytnyt ngcngcngtn wsnytngaym gntayytngc nytngtncay    540
ccnytnmgng cnmgngcnyt nmgnggnmgn mgnytngcny tnggnytntg yatggcngcn    600
tggytnatgg cngcngcnyt ngcnytnccn ytnacnytnc armgncarac nttymgnytn    660
gcnmgnwsng aymgngtnyt ntgycaygay gcnytnccny tngaygcnca rgcnwsncay    720
tggcarccng cnttyacntg yytngcnytn ytnggntgyt tyytnccnyt nytngcnatg    780
ytnytntgyt ayggngcnac nytncayacn ytngcngcnw snggnmgnmg ntayggncay    840
gcnytnmgny tnacngcngt ngtnytngcn wsngcngtng cnttyttygt nccnwsnaay    900
ytnytnytny tnytncayta ywsngayccn wsnccnwsng cntggggnaa yytntayggn    960
gcntaygtnc cnwsnytngc nytnwsnacn ytnaaywsnt gygtngaycc nttyathtay   1020
taytaygtnw sngcngartt ymgngayaar gtnmgngcng gnytnttyca rmgnwsnccn   1080
ggngayacng tngcnwsnaa rgcnwsngcn garggnggnw snmgnggnat gggnacncay   1140
wsnwsnytny tncar                                                   1155

<210> SEQ ID NO 4
<211> LENGTH: 7
<212> TYPE: PRT
<213> ORGANISM: Artificial Sequence
<220> FEATURE:
<223> OTHER INFORMATION: Peptide.

<400> SEQUENCE: 4

Ile Thr Thr Cys His Asp Val
  1               5
```

<210> SEQ ID NO 5
<211> LENGTH: 42
<212> TYPE: PRT
<213> ORGANISM: Artificial Sequence
<220> FEATURE:
<223> OTHER INFORMATION: Polypeptide.

<400> SEQUENCE: 5

```
Met Asp Ser Lys Gly Ser Ser Gln Lys Gly Ser Arg Leu Leu Leu Leu
 1               5                  10                  15

Leu Val Val Ser Asn Leu Leu Leu Cys Gln Gly Val Val Ser Asp Tyr
                20                  25                  30

Lys Asp Asp Asp Lys Leu Glu Gly Gly
            35                  40
```

<210> SEQ ID NO 6
<211> LENGTH: 8
<212> TYPE: PRT
<213> ORGANISM: Artificial Sequence
<220> FEATURE:
<223> OTHER INFORMATION: Peptide.

<400> SEQUENCE: 6

```
Asp Tyr Lys Asp Asp Asp Asp Lys
 1               5
```

<210> SEQ ID NO 7
<211> LENGTH: 6
<212> TYPE: PRT
<213> ORGANISM: Artificial Sequence
<220> FEATURE:
<223> OTHER INFORMATION: Peptide.

<400> SEQUENCE: 7

```
Gly Tyr Pro Gly Gln Val
 1               5
```

<210> SEQ ID NO 8
<211> LENGTH: 6
<212> TYPE: PRT
<213> ORGANISM: Artificial Sequence
<220> FEATURE:
<223> OTHER INFORMATION: Peptide.

<400> SEQUENCE: 8

```
Ser Phe Leu Leu Arg Asn
 1               5
```

<210> SEQ ID NO 9
<211> LENGTH: 22
<212> TYPE: DNA
<213> ORGANISM: Artificial Sequence
<220> FEATURE:
<223> OTHER INFORMATION: Primer.

<400> SEQUENCE: 9
tggcactgcc cctgacactg ca                                           22

<210> SEQ ID NO 10
<211> LENGTH: 20
<212> TYPE: DNA
<213> ORGANISM: Artificial Sequence
<220> FEATURE:
<223> OTHER INFORMATION: Primer.

<400> SEQUENCE: 10

-continued cccgtagcac agcagcatgg                                              20

<210> SEQ ID NO 11
<211> LENGTH: 18
<212> TYPE: DNA
<213> ORGANISM: Artificial Sequence
<220> FEATURE:
<223> OTHER INFORMATION: Primer.

<400> SEQUENCE: 11
ggtgcccgcc ctctatgg                                                18

<210> SEQ ID NO 12
<211> LENGTH: 18
<212> TYPE: DNA
<213> ORGANISM: Artificial Sequence
<220> FEATURE:
<223> OTHER INFORMATION: Primer.

<400> SEQUENCE: 12
tcgcgaggtt catcagca                                                18

<210> SEQ ID NO 13
<211> LENGTH: 9
<212> TYPE: DNA
<213> ORGANISM: Artificial Sequence
<220> FEATURE:
<223> OTHER INFORMATION: Illustrative nucleotide sequence.

<400> SEQUENCE: 13 atgcacggg                                                          9

<210> SEQ ID NO 14
<211> LENGTH: 9
<212> TYPE: DNA
<213> ORGANISM: Artificial Sequence
<220> FEATURE:
<223> OTHER INFORMATION: Illustrative nucleotide sequence.

<400> SEQUENCE: 14 cccgtgcat                                                          9

<210> SEQ ID NO 15
<211> LENGTH: 12
<212> TYPE: DNA
<213> ORGANISM: Artificial Sequence
<220> FEATURE:
<223> OTHER INFORMATION: Illustrative nucleotide sequence.

<400> SEQUENCE: 15
atggcttagc tt                                                      12

<210> SEQ ID NO 16
<211> LENGTH: 12
<212> TYPE: DNA
<213> ORGANISM: Artificial Sequence
<220> FEATURE:
<223> OTHER INFORMATION: Illustrative nucleotide sequence.

<400> SEQUENCE: 16
tagcttgagt ct                                                      12

<210> SEQ ID NO 17
<211> LENGTH: 12
<212> TYPE: DNA
<213> ORGANISM: Artificial Sequence

```
<220> FEATURE:
<223> OTHER INFORMATION: Illustrative nucleotide sequence.

<400> SEQUENCE: 17
gtcgactacc ga                                                              12

<210> SEQ ID NO 18
<211> LENGTH: 25
<212> TYPE: PRT
<213> ORGANISM: Artificial Sequence
<220> FEATURE:
<223> OTHER INFORMATION: PAR1 polypeptide.

<400> SEQUENCE: 18

Thr Leu Asp Pro Arg Ser Phe Leu Leu Arg Asn Pro Asn Asp Lys Tyr
 1               5                  10                  15

Glu Pro Phe Trp Glu Asp Glu Glu Lys
            20                  25

<210> SEQ ID NO 19
<211> LENGTH: 25
<212> TYPE: PRT
<213> ORGANISM: Artificial Sequence
<220> FEATURE:
<223> OTHER INFORMATION: PAR2 polypeptide.

<400> SEQUENCE: 19

Ser Ser Lys Gly Arg Ser Leu Ile Gly Lys Val Asp Gly Thr Ser His
 1               5                  10                  15

Val Thr Gly Lys Gly Val Thr Val Glu
            20                  25

<210> SEQ ID NO 20
<211> LENGTH: 24
<212> TYPE: PRT
<213> ORGANISM: Artificial Sequence
<220> FEATURE:
<223> OTHER INFORMATION: PAR3 polypeptide.

<400> SEQUENCE: 20

Thr Leu Pro Ile Lys Thr Phe Arg Gly Ala Pro Pro Asn Ser Phe Glu
 1               5                  10                  15

Glu Phe Pro Phe Ser Ala Leu Glu
            20

<210> SEQ ID NO 21
<211> LENGTH: 25
<212> TYPE: PRT
<213> ORGANISM: Artificial Sequence
<220> FEATURE:
<223> OTHER INFORMATION: PAR4 polypeptide.

<400> SEQUENCE: 21

Leu Pro Ala Pro Arg Gly Tyr Pro Gly Gln Val Cys Ala Asn Asp Ser
 1               5                  10                  15

Asp Thr Leu Glu Leu Pro Asp Ser Ser
            20                  25
```